United States Patent [19]

Matsuda et al.

[11] 3,973,127
[45] Aug. 3, 1976

[54] X-RAY TOMOGRAPHY APPARATUS

[75] Inventors: Tadayoshi Matsuda, Tokyo; Mitsuo Yuasa, Yokohama; Kenji Aoyama, Kawasaki, all of Japan

[73] Assignee: Tokyo Shibaura Electric Co., Ltd., Kawasaki, Japan

[22] Filed: Oct. 6, 1975

[21] Appl. No.: 619,963

[30] Foreign Application Priority Data
 Oct. 9, 1974   Japan.............................. 49-116436
 Aug. 15, 1975  Japan.............................. 50-99373
 Aug. 15, 1975  Japan.......................... 50-112706[U]

[52] U.S. Cl. ............................ 250/445 T; 250/320; 250/511; 250/525
[51] Int. Cl.² ................................................ G01N 23/02
[58] Field of Search ................ 250/445 T, 320, 511, 250/525

[56] References Cited
UNITED STATES PATENTS

| 3,783,282 | 1/1974 | Hoppenstein | 250/313 |
| 3,790,782 | 2/1974 | Inone et al. | 250/445 T |
| 3,922,552 | 11/1975 | Ledley | 250/445 T |
| 3,934,142 | 1/1976 | Hounsfield | 250/445 T |

*Primary Examiner*—Alfred E. Smith
*Assistant Examiner*—Bruce C. Anderson
*Attorney, Agent, or Firm*—Finnegan, Henderson, Farabow & Garrett

[57] ABSTRACT

An X-ray tomography apparatus includes an X-ray tube, a collimator device and a film, which are revolved about an object body of medical examination in the same direction and at the same speed. The collimator device and the film are also rotated about their axes in the same direction and at the same speed.

11 Claims, 21 Drawing Figures

X-RAY TOMOGRAPHY APPARATUS

This invention relates to an X-ray tomography apparatus and more particularly to an X-ray tomography apparatus wherein an X-ray source and a photographic film are rotated at the same time about the axial line of an object body of medical examination placed on a seat board.

The X-ray tomography apparatus in common use causes an X-ray source to revolve about the axial line of an examinee's body and also a photographic film to revolve about said axial line in the same direction and at the same speed as the X-ray source while making its own rotation, and continuously takes photographs under this condition so as to project the cross section of the examinee's body distinctly on a simple film with the image of the peripheral portion of the cross section of the examinee's body purposely vignetted.

With such type of X-ray tomography apparatus, an iris diaphragm or collimator is provided ahead of an X-ray source, for example, an X-ray tube so as to effectively project an X-ray flux emitted from said tube on a film and limit the field of X-ray irradiation in accordance with the shape and size of the film in order to prevent the examinee's unnecessary exposure to X-rays. In this case, the opening area of the collimator device which is controlled by diaphragm blades is always fixed parallel with the cross sectional plane of X-ray flux. Since the film momentarily changes its direction relative to the examinee's body as the result of its revolution, it is almost impossible on principle for the X-ray tomography apparatus of the above-mentioned arrangement in which the diaphragm opening is fixed parallel with the cross sectional plane of X-ray flux to cause said opening to be diaphragmed exactly in accordance with the shape and size of the film used. Since, as mentioned above, the film momentarily changes its direction relative to the examinee's body as the result of its revolution, the X-ray flux is projected on the film at a prescribed angle. With, therefore, an actually rectangular film taken to have a circular form whose diameter is represented by the lengthwise axis of the film, the customary practice is to design the opening of the collimator device to have a prescribed elliptic shape or a rectangular shape abutting against the outer periphery of said prescribed elliptic shape. Moreover, it is necessary to select the shape and size of a film used according to the various portions of an examinee's body subjected to X-ray photography, for example, the head and chest. In practice, therefore, the configuration of the X-ray irradiation field is changed through proper exchange of the blades of the collimator device. In any case, it is impossible to attain accurate agreement between the X-ray irradiation field and the shape and size of the film used. It is impossible to limit the field of X-ray flux irradiation only to the affected portion which generally lies in a local spot on the cross section of the examinee's body, that is, outside of the center of said cross section. Undue broadening of the cross section of X-ray flux results in the corresponding increase in the field through which X-rays are irradiated on the examinee's body and consequently the examinee's unnecessary exposure to X-rays. Now let it be assumed that an X-ray film has a quarter size (10 × 12 inches) and the X-ray flux is so ideally throttled as to be projected only on the surface of the film. Then the area $S_1$ of the field of X-ray irradiation may be expressed as:

$$S_1 = 10 \times 12 \text{ in.} = 120 \text{ square inches}$$

Where, however, the opening of the collimator device is diaphragmed into an elliptic shape to provide a circular field of X-ray irradiation for the film, then the area $S_2$ of said field may be indicated as:

$$S_2 = \frac{\pi}{4} \sqrt{10^2+12^2} = \frac{\pi}{4} \sqrt{244} = 192 \text{ (square inches)}$$

That is, $S_2$ will be increased over 1.5 times $S_1$. Further, the examinee's unnecessary exposure to X-rays leads to the increased scattering of X-rays from the examinee's body, and consequently the decreased picture quality of X-ray photographs taken of the cross section of the examinee's body.

Now let it be assumed that an X-ray flux is diaphragmed on the surface of a film, for example, on a 5-centimeter radius circular affected portion which is centered at a point 10 centimeters apart from the film center. Then the area $S_1'$ of said X-ray flux irradiation field may be expressed by the following equation:

$$S_1' = \pi \times 5^2 = 25\pi \text{ (square centimeters)}$$

However, with the prior art collimator device which carries out diaphragming in parallel with the cross section of an irradiated X-ray flux, the area $S_2'$ of the field of X-ray flux irradiation will be prominently increased to 9 times $S_1'$ as indicated by the following equation:

$$S_2' = \pi \times (10+5)^2 = 225\pi \text{ (square centimeters)}$$

It is accordingly the object of this invention to provide an X-ray tomography apparatus which can diaphragm an X-ray fluxes so as to attain accurate agreement between the field of X-ray irradiation and the shape and size of an X-ray film used simply by conforming the configuration of the opening of the collimator device with the shape and size of the X-ray film.

The other object of this invention is to provide a device which can limit the field of X-ray flux irradiation only to the affected portion generally lying in a local spot on the cross section of the examinee's body, that is, outside of the center of said cross section.

According to an aspect of this invention, there is provided an X-ray tomography apparatus comprising a seat board for seating an object body of medical examination having a cross section requiring X-ray tomography; an X-ray source for irradiating X-rays toward said examinee's body; collimator means disposed between said X-ray source and seat board and provided with an opening parallel with the cross section of the examinee's body for restricting the cross section of an X-ray flux emitted from the X-ray source to prescribed dimensions; film-supporting means for holding a film photographing X-ray images of the cross section of the examinee's body from the X-ray flux passing through said cross section in parallel relationship therewith; and drive mechanism for causing the X-ray source, collimator means and film to revolve about the examinee's body in the same direction and at the same speed and also causing the collimator means and film to rotate about their axes at the same speed.

This invention can be more fully understood from the following detailed description when taken in conjunction with the accompanying drawings, in which.

Figure 1:
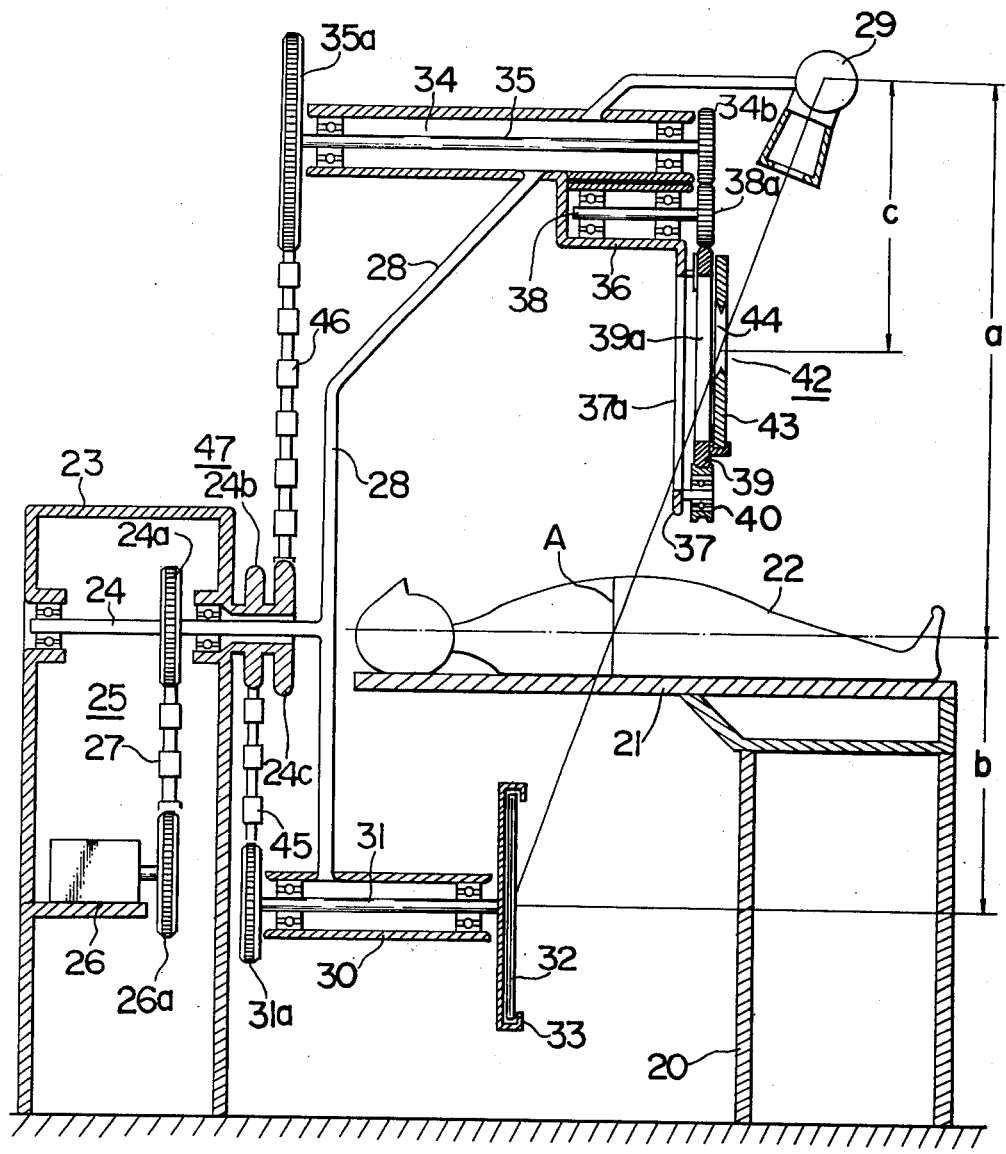
FIG. 1 is a schematic cross sectional view of an X-ray tomography apparatus embodying this invention.
Figure 3:
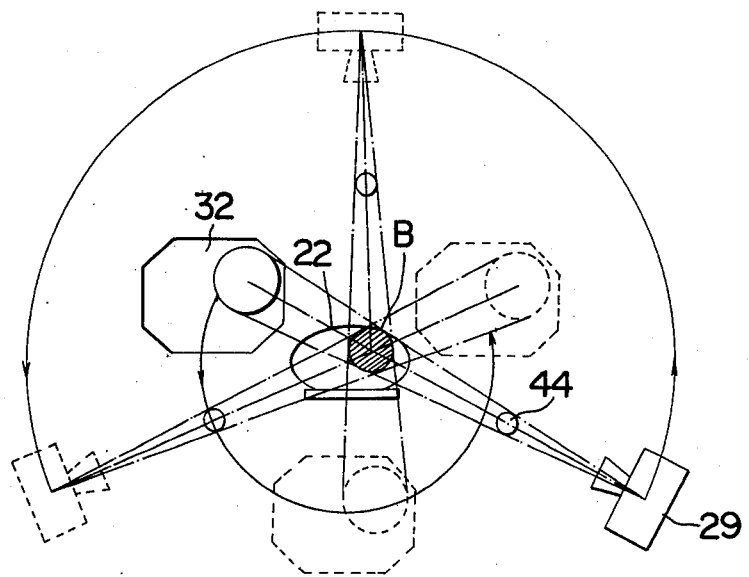
Figure 4A:
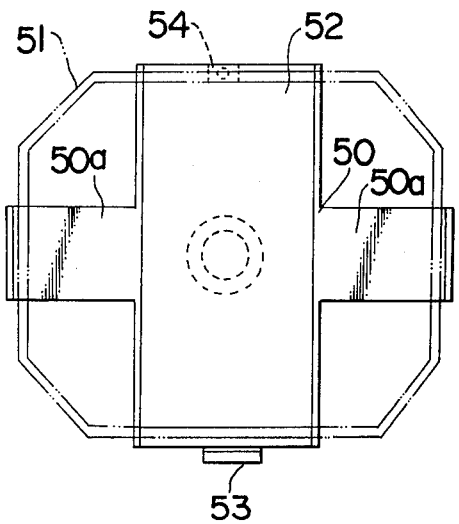
Figure 4B:
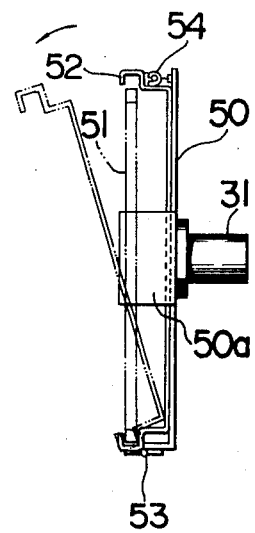
Figure 5:
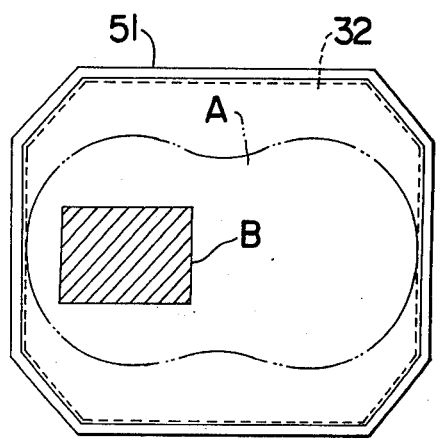
Figure 6:
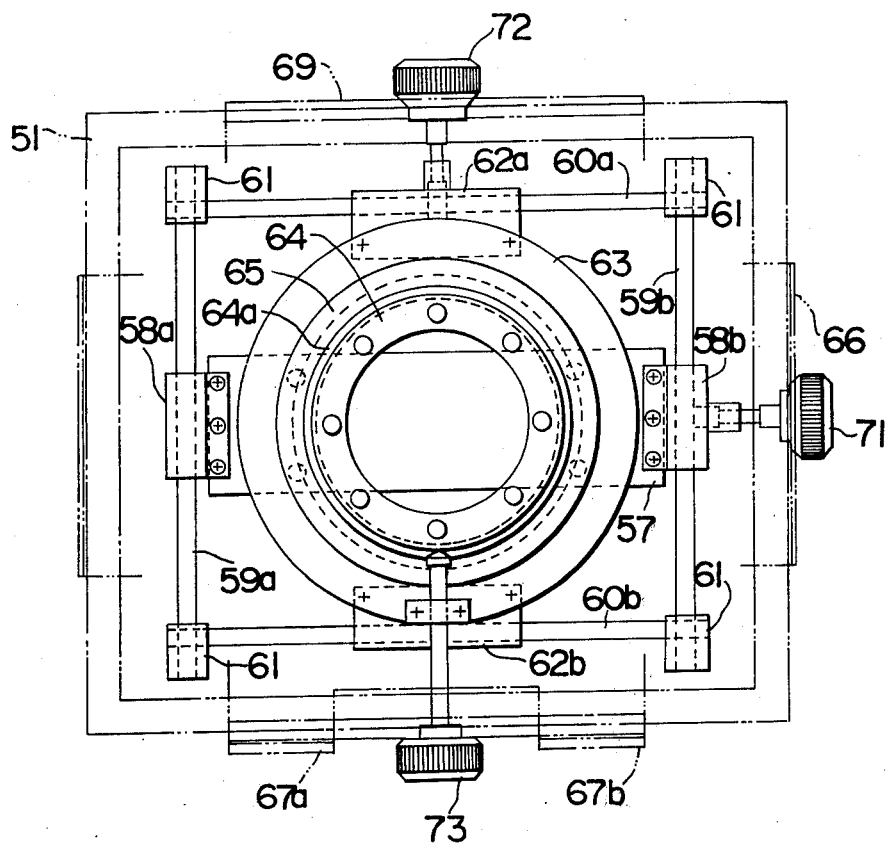
Figure 7:
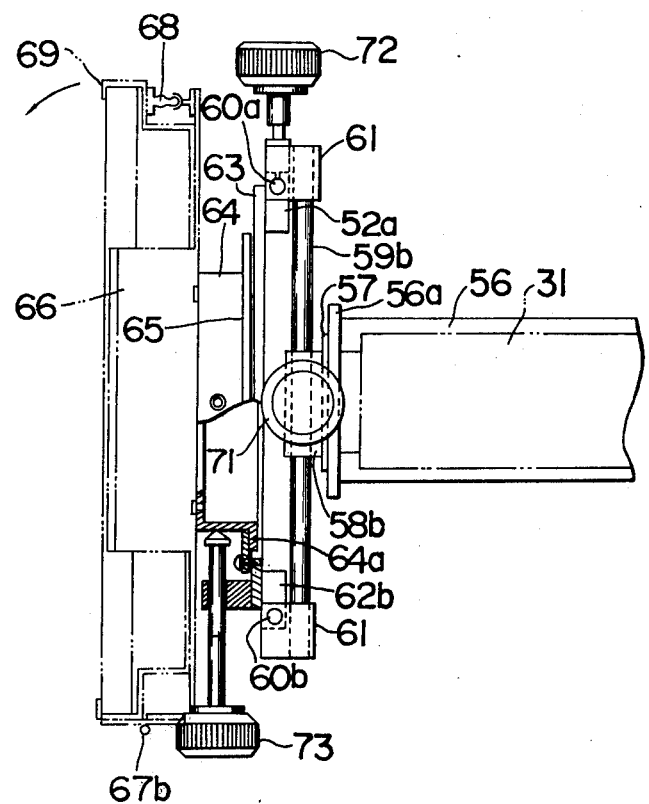
Figure 8:
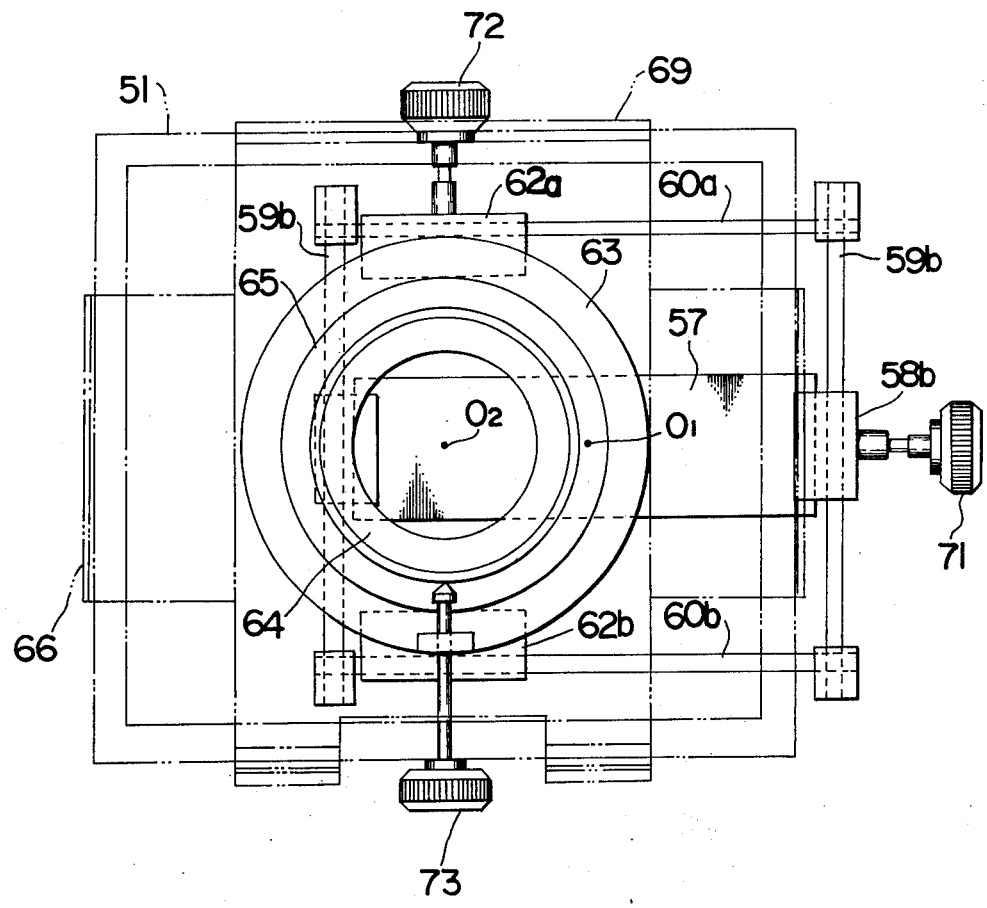
Figure 9:
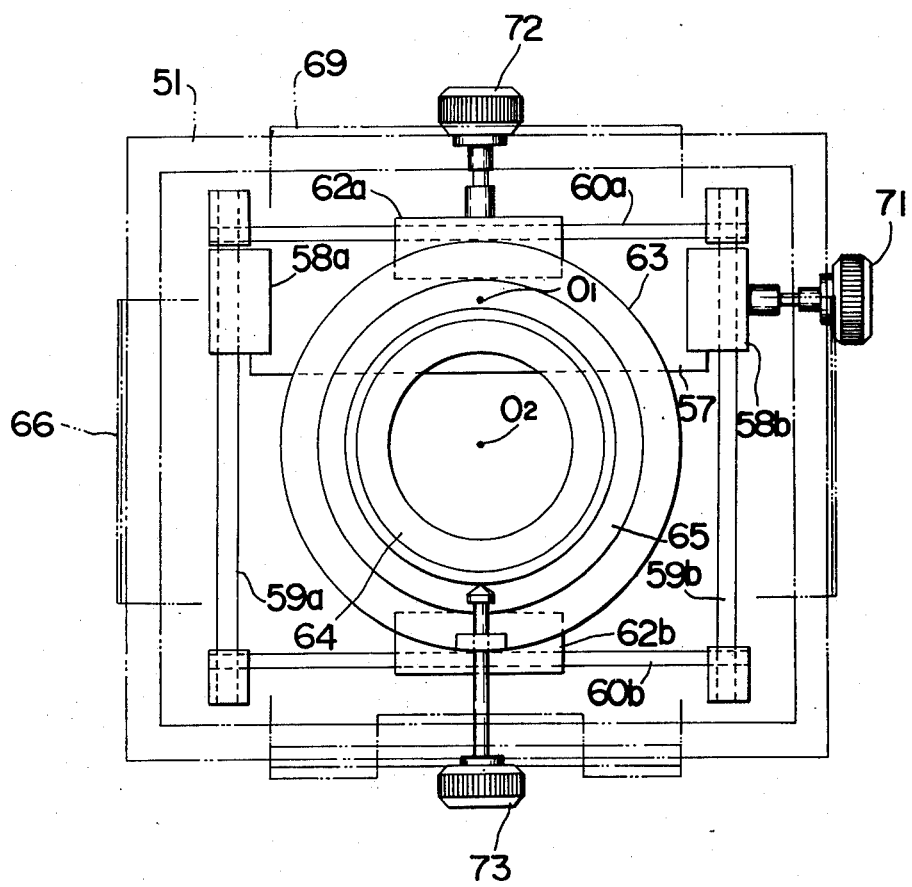

FIG. 3 schematically shows the relative positions of an X-ray source and a film when a tomographic picture is taken of an examinee's body by the apparatus of FIG. 1;

FIGS. 4A and 4B and FIG. 5 jointly illustrate a cassette holder for use with the apparatus of FIG. 1: FIG. 4A is a front view of said cassette holder, FIG. 4B is a side view thereof, and FIG. 5 indicates the relative positions of an X-ray film and a photographed image;

FIGS. 6 to 9 jointly show another form of cassette holder; FIG. 6 is a front view thereof, FIG. 7 is a side view thereof, partly in section, and FIGS. 8 and 9 are front views of said cassette holder showing its different operating conditions.

Figure 12:
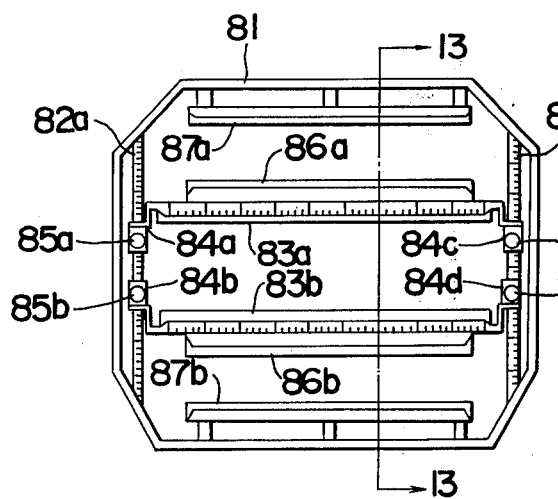
Figure 13:
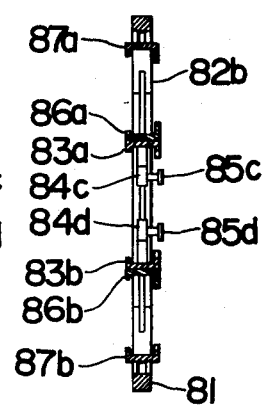
Figure 14A:
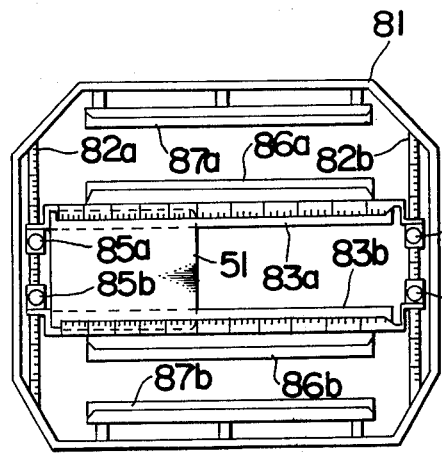
Figure 14B:
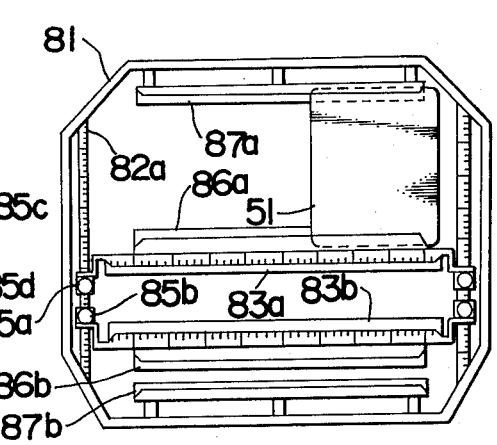
Figure 15:
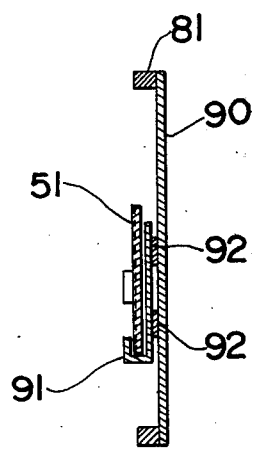
Figure 16:
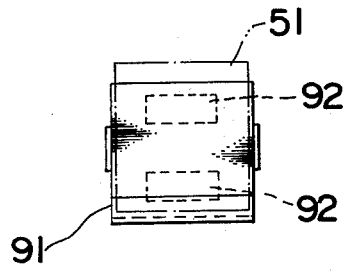

FIG. 10 and FIGS. 11A to 11D present the relative positions of photographed images and an X-ray film when a tomographic picture is taken of the cross section of an examinee's body by the apparatus shown in FIGS. 6 to 9;

FIGS. 12, 13, 14A and 14B jointly set forth another form of cassette holder: FIG. 12 is a front view thereof, FIG. 13 is a sectional view on line 13—13 of FIG. 12, and FIGS. 14A and 14B are the same front views of said cassette holder as FIG. 12, presenting its different operating conditions; and FIGS. 15 and 16 show still another form of cassette holder: FIG. 15 is a sectional view thereof, and FIG. 16 is a front view thereof.

There will now be described by reference to the appended drawings an X-ray tomography apparatus embodying this invention. As shown in FIG. 1, the subject X-ray tomography apparatus is provided with a pedestal 20 on the top of which a horizontally extending seat board 21 is mounted to carry an object body 22 of medical examination. A fixed stand 23 is provided on one side of the seat board 21. One end of a support shaft 24 rotatably fitted to the stand 23 horizontally extends to that side of said stand 23 which faces the seat board 21. The support shaft 24 is rotated at a constant speed by a drive mechanism 25 received in the stand 23. Said drive mechanism 25 comprises a first sprocket 24a rotatably fitted to the intermediate part of the support shaft 24, a motor 26 disposed in the stand 23, a second sprocket 26a fixed to the rotary shaft of the motor 26 and a chain 27 stretched across both sprockets 24a, 26a so as to transmit the rotating moment of the motor 26 to the support shaft 24.

Figure 2:
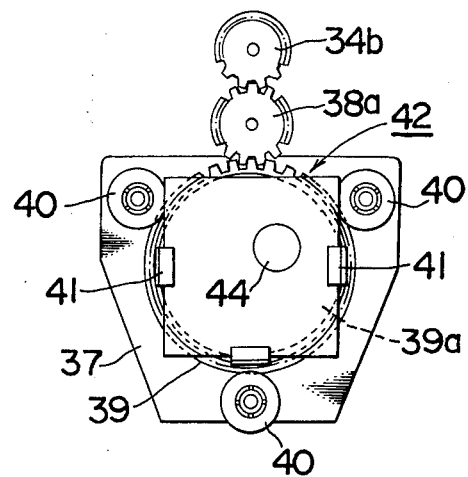
FIG. 2 is a front view of the collimator device of the X-ray tomography apparatus of FIG. 1.

Integrally fitted to the extending end of the support shaft 24 is the intermediate part of a horizontal support arm 28, one end of which is bent in a direction departing from the fixed stand 23. An X-ray tube 29 is fixed to the end of the bent portion of the support arm 28 so as to emit X-rays on that portion of the body of the examinee 22 placed on the seat board 21 which is to be subjected to X-ray tomography. A cylindrical member 30 provided with a bearing and extending parallel with the seat board 21 is fixed to the other end of the support arm 28. A rotary shaft 31 extending lengthwise of said cylindrical member 30 is supported on the bearing. An X-ray film 32 is held on that side of the rotary shaft 31 which faces the pedestal 20 by the later detailed cassette holder 33 in a vertical position, that is, parallel with the cross sectional plane A of that portion of an examinee's body which is to be subjected to X-ray tomography. A third sprocket 31a is concentrically fixed to the other end of the rotary shaft 31. A cylindrical member 34 provided with a bearing and extending parallel with the seat board 21 is fixed to the bent portion of the support arm 28. A horizontally extending rotary shaft 35 is rotatably supported in said cylindrical member 34. Fitted to that end of the cylindrical member 34 which faces the seat board 21 are an auxiliary cylindrical member 36 provided with a bearing and a support plate 37 vertically extending toward the seat board 21 and bored with an opening 37a at the center. The inner end of the rotary shaft 35 is fitted with a drive gear 34b, which in turn engages an intermediate gear 38a rotatably fitted to the inner end of said auxiliary cylindrical member 36 through a shaft 38. A driven gear 39 provided with an opening 39a at the center is disposed parallel in front of the support plate 37 so as to be engaged with the intermediate gear 38a. Said driven gear 39 is rotatably supported on the support plate 37 by cog wheels 40 which are positioned, as shown in FIG. 2, 120° apart from each other, rotatably fitted to the front side of the support plate 37 and engaged with the driven gear 39. Each cog wheel 40 has a flanged portion formed on the peripheral walls of both sides, said flanged portions supporting the driven gear 39 from both sides thereof, thereby restricting the shift of the driven gear 39 in the direction of its thickness. An iris diaphragm device or collimator device 42 is fixed in front of the driven gear 39 through fitting metal parts 41. Said collimator device 42 is a known type in which the diaphragm opening 44 has its shape and size adjusted by diaphragm blades 43 (FIG. 1). As the result, an X-ray flux emitted from the X-ray tube 29 is diaphragmed by the opening 44 of the collimator device 42 so as to have a prescribed cross section and is projected on an examinee's body through the opening 39a of the driven gear 39 and the opening 37a of the support plate 37.

A fourth sprocket 35a is concentrically fixed to the other or rear end of the rotary shaft 35 rotatably supported by the cylindrical member 34. Fifth and sixth stational sprockets 24b, 24c are fixed to the stationary stand 23 to be concentric with the support shaft 24 rotatably fitted to the stationary stand 23. Both sprockets 24b, 24c respectively have the same number of teeth as the sprocket 31a and the sprocket 24c. As the result, the drive of the motor 26 causes the X-ray tube 29 and film 32 to be revolved by the vertical arm 28 about the support shaft 24, namely, about the longitudinal axis of an examinee's body in the same direction and at the same speed. In this case, the collimator device 42 and film 32 make their own rotation in the same direction by the rotation of the arm 28. The first to sixth sprockets constituting the drive-transmitting mechanism 47 and associated gears have a prescribed gear ratio in order to attain the revolution of the X-ray tube 29 and film 32 and the rotation of the collimator device 42 and film 32 at the same speed.

With the X-ray tomography apparatus arranged as described above, the X-ray tube 29, film 32 and collimator device 42 make revolutions and/or rotations in the aforesaid relationship. If, therefore, the opening 44 of the collimator device 42 is made similar to the shape of the film 32, then the X-ray flux emitted from the X-ray tube 29 is projected on the film 32 through the field of X-ray irradiation having the same shape as said film 32 even while the X-ray tube 29 and film 32 revolve about an examinee's body 22, provided a proper distance is allowed between the X-ray tube 29 and the examinee's body 22 as well as between the examinee's body 22 and film 32. Now, as shown in FIG. 1, let the character $a$ denote a distance between the focal point of the X-ray tube 29 and the longitudinal axis of the examinee's body 22, that is, the rotation axis of the support shaft 24, the character $b$ show a distance between the rotation axis of said support shaft 24 and the rotation axis of the film 32, and the character $c$ represent a distance between the focal point of the X-ray tube 29 and the rotation axis of the collimator device 42. Then, it is advised to cause the opening 44 of the collimator device 42 to bear a reduced scale ratio $c/(a+b)$ to the size of the film 32. This arrangement minimizes X-ray dosage to the examinee's body 22 and consequently harmful effect on him and the scattering of X-rays from him, thereby providing a distinct tomographical picture in good contrast.

If the subject X-ray tomography apparatus is operated with the opening 44 of the collimator device 42 so diaphragmed as to conform with the affected spot B of the cross section of an examinee's body 22, then X-rays can be irradiated only on said affected spot B, providing a good tomographical picture thereof freer from scattered X-rays.

Also, in the X-ray tomography apparatus described above, the sprockets 31a, 35 rotating the film 32 and collimator device 42 are driven by the arm 28, chains 45, 46 and stationary sprockets 24b, 24c, a servo-motor may be used to rotate the film 32 and collimator device 42 in synchronism with the revolution of the film 32, collimator device 42 and X-ray tube 29.

The cassette holder for supporting the film 32 may consist of the known type arranged, for example, as follows.

Referring to FIGS. 4A and 4B, a first cassette-supporting plate 50 fitted to the forward end of the film rotary shaft 31 has a pair of elongate plate members 50a extending toward both horizontal sides of said film-supporting plate 50. The outer ends of said paired elongate plate members 50a are provided with projections which clamp a cassette 51 carrying an X-ray film from both horizontal sides. Disposed parallel with the first cassette-supporting plate 50 in a second cassette-supporting plate 52 which is provided with projections at the upper and lower ends so as to vertically clamp the cassette 51. The second cassette-supporting plate 52 is provided with a hinge 53 at the lower end and swingably fitted to the lower end of the first cassette-supporting member 50. Both cassette-supporting plates 50, 52 are normally kept in parallel relationship by a ball-catcher mechanism 54 extending across the top portions of said supporting plates 50, 52.

Where the cassette 51 is loaded in the cassette-supporting device arranged as described above, the second cassette-supporting plate 52 is first swung outward, as shown in FIG. 4B, in the direction of the indicated arrow to take a position defined by two dots-chain phantom lines. Thereafter, the cassette 51 is fitted into the second cassette-supporting plate 52, which is now swung counterclockwise to be disposed parallel with the first cassette-supporting plate 50 by means of the aforesaid ball-catcher mechanism 54. As the result, both horizontal side edges of the cassette 51 are engaged with the engagement members of the first cassette-supporting plate 50, and the upper and lower edges of the cassette 51 are engaged with the engagement members of the second cassette-supporting plate 52, thereby causing the cassette 51 to be loaded vertically parallel with both supporting plates 50, 52.

The above-mentioned cassette-supporting device indeed has the advantages that it has a simple arrangement and is easily loaded and removed, but is accompanied with the undermentioned drawbacks when a photograph is taken by the X-ray tomography apparatus with the opening 44 of the collimator device 42 diaphragmed to a prescribed extent. Namely, even where, as shown in FIG. 5, only the effected spot B of the cross section A of an examinee's body 22 indicated in a two-dots chain line is photographed, an X-ray film 32 large enough to conform with the cassette 51 whose outline is shown in a broken line has to be used, resulting in great economic disadvantage. In the case of tomography, a plurality of tomographic pictures are generally taken with the position of the camera shifted at a suitable interval in the axial direction of the examinee's body 22 so as to provide a stereoscopic image of the affected spot B. In such case, wasted portions of X-ray films are prominently larger.

To avoid such waste of X-ray films, the undermentioned cassette-supporting device shown in FIGS. 6 to 9 offers great convenience. This cassette-supporting device is engaged with the rotary shaft 31 of an X-ray film shown in FIG. 1 to be rotated therewith. Therefore, said cassette-supporting device has a rotary shaft 56 (FIG. 7) rotatable in synchronization with the rotation of the support arm 28. The end of said rotary shaft 56 is provided with a rectangular flanged portion 56a. Disposed ahead of the flanged portion 56a is a rectangular connection board 57 (FIG. 9), both lengthwise ends of which are provided with first guide bearings 58a, 58b. First guide shafts 59a, 59b are so supported on the guide bearings 58a, 58b as to extend parallel in the same plane crosswise of the connection board 57, and move in the axial direction. A pair of second guide shafts 60a, 60b are bridged across both ends of each of the first guide shafts 59a, 59b by connection blocks 61 so as to be disposed perpendicular to said first guide shafts 59a, 59b. The second guide shafts 60a, 60b are provided with second guide bearings 62a, 62b respectively which are made to slide in the axial direction of said second guide shafts 60a, 60b. The mutually facing end portions of a disc-like rotary drum-supporting board 63 are fixed to the second guide bearings 62a, 62b, thus enabling said disc-like supporting board 63 to be moved along the second guide shafts 60a, 60b. Positioned ahead of the disc-like supporting board 63 is a rotary drum 64 provided with a flanged portion 64a so as to rotate about the central axis by a keep plate 65 which is bored with an opening slightly larger than the outer diameter of said drum 64 and clamps said flanged portion 64a between the supporting board 63 and said keep plate 65. Fitted ahead of the rotary drum 64 is a cassette-supporting device having the same arrangement as that of FIGS. 4A and 4B. The cassette-supporting device of FIGS. 6 to 9 comprises a first cassette-supporting plate 66 for holding the cassette 51 at both horizontal sides thereof through engagement members and a second cassette-supporting plate 69, the lower end portion of which is hinged to the lower end portion of the first cassette-supporting plate 66 by hinges 67a, 67b and the upper end portion of which is provided with a ball catcher mechanism 68 so as to be engaged with the upper end portion of the first cassette-supporting plate 66. The second cassette-supporting plate 69 has the upper and lower end portions bent in the L-shape. These L-shaped bent portions are engaged with the cassette 51 so as to clamp it vertically. Referential numeral 71 denotes a fixing screw threadedly engaged with the first guide bearing 58b so as to secure it to the first guide shaft 59B, the inner end of said screw 71 being pressed against the first guide shaft 59b. Referential numeral 72 shows a fixing screw for securing the second guide bearing 62a to the second guide shaft 60a. Referential numeral 73 indicates a fixing screw threadedly engaged with the disc-like rotary drum-supporting board 63 so as to restrict the rotation of the rotary drum 64 by having the inner end of said screw 73 pressed against the peripheral wall of said rotary drum 64.

Where, in the cassette-supporting device of the abovementioned arrangement, the fixing screw 72 is loosened to allow the second guide bearings 62a, 62b to be moved along the second guide shafts 60a, 60b, for example, in the opposite direction to the fixing screw 71, then the center $O_2$ of the cassette 51 can be displaced leftward, as shown in FIG. 8, relative to the rotation center $O_1$ of the rotary shaft 56. Where the fixing screw 71 is loosened to allow the first guide shafts 59a, 59b to be brought downward relative to the first guide bearings 58a, 58b, then the center $O_2$ of the cassette 51 can be displaced downward, as shown in FIG. 9, relative to the rotation center $O_1$ of the rotary shaft 56. A proper combination of the horizontal and vertical displacements of the cassette 51 can freely change the position of its center $O_2$.

Figure 10:
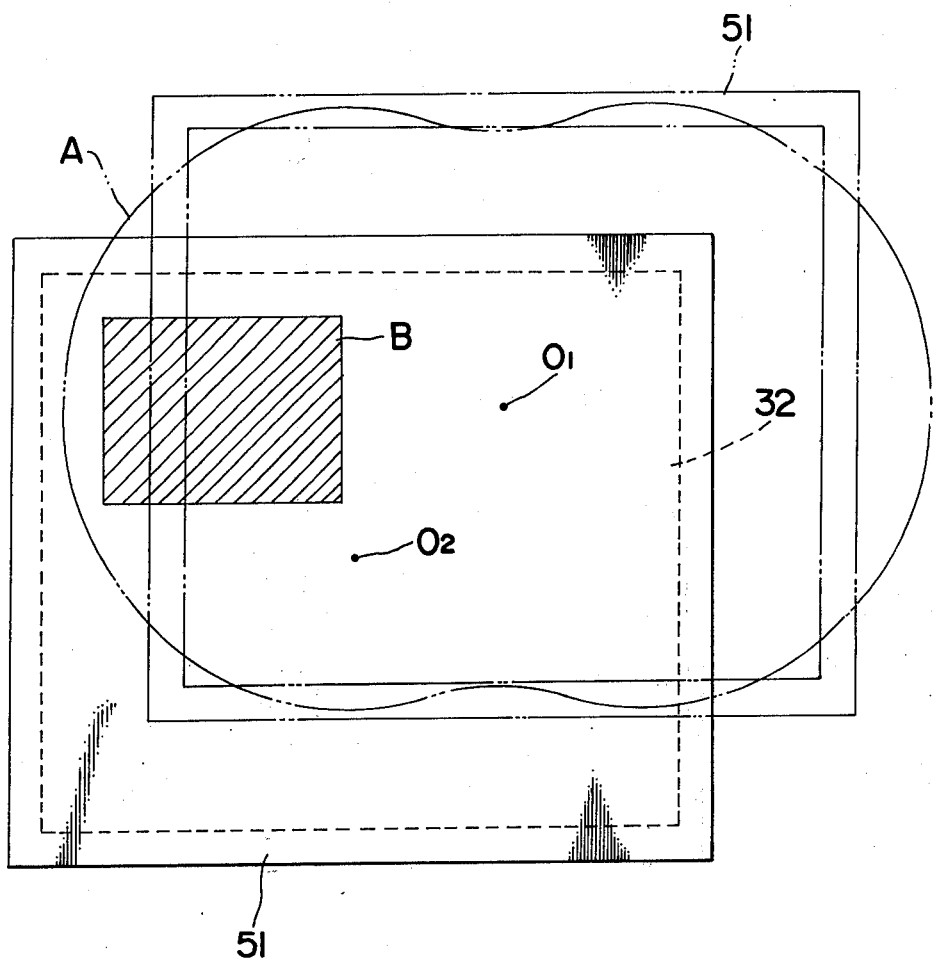
Figure 11A:
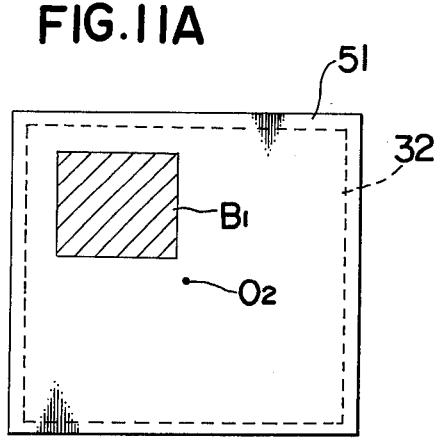
Figure 11B:
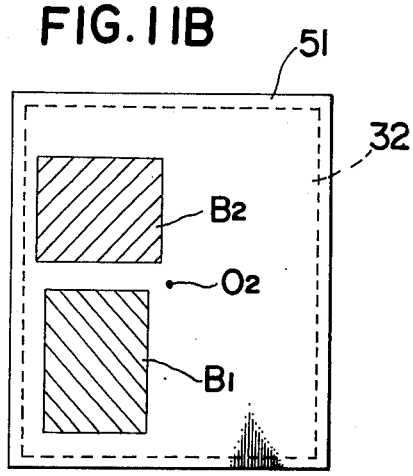
Figure 11C:
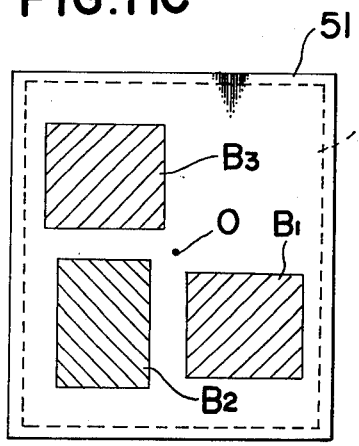
Figure 11D:
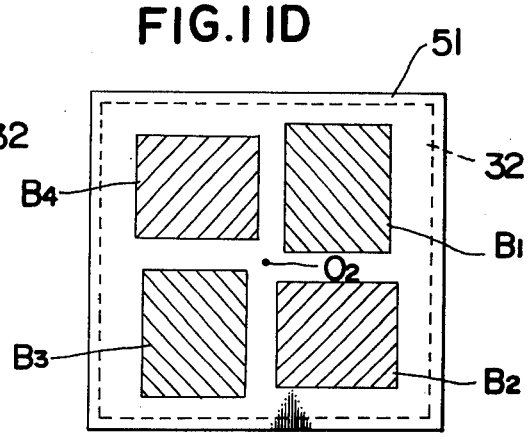

There will now be described the case where the cassette-supporting device of FIGS. 6 to 9 is used with the X-ray tomography apparatus of FIG. 1 and the affected spot of the cross section of an examinee's body 22 positioned apart from the central axis of said body is subjected to X-ray tomography. Where four pictures are taken of the affected spot B of the cross section A of an examinee's body 22 by shifting the camera at a suitable interval in the axial direction of the examinee's body 22 and are projected on a single film, then a cassette 51 should be provided which carries a film 32 about four times as large as said affected spot B (FIG. 10). The second cassette-supporting plate 69 is swung in the direction of the arrow indicated in FIG. 7. The cassette 51 is fitted into said second cassette-supporting plate 69 thus swung so as to vertically clamp the cassette 51 by engagement members. Thereafter, the second cassette-supporting plate 69 is swung backward counterclockwise to be positioned parallel with the first cassette-supporting plate 66 by means of the ball-catcher mechanism 68. As the result, the cassette 51 has its both horizontal side edges supported on the first cassette-supporting plate 66 by its engagement members.

Where the center of the cassette 51 falls on the center $O_1$ of the rotary shaft 56 for the film as shown in two dots-chain lines, then the image of the affected spot B protrudes from the outline of the cassette 51. However, the cassette 51 is so shifted (at this time the center of the cassette 51 is indicated by $O_2$) by the aforesaid operation of the fixing screws 71, 72 as to cause the image of the affected spot B to take the upper left position on the cassette 51. Under this condition, a first picture is taken of the affected spot B and the tomographic image $B_1$ is projected on the upper left section of the film 32 as illustrated in FIG. 11A. Then the examinee's body 22 is shifted for a prescribed distance along its axis. At this time, the fixing screw 73 is loosened, the first and second cassette-supporting plates 66, 69 are swung 90° counterclockwise, the fixing screw 73 is tightened again, and the film 32 is shifted 90° counterclockwise. Under this condition, a second picture is taken of the affected spot B and the tomographic image $B_2$ is projected on the upper left section of the film 32. Similarly, each time a picture is taken of the affected spot B, the cassette 51 is swung 90° counterclockwise, and the examinee's body 22 is shifted in its axial direction. Then, a third tomographic image $B_3$ and a fourth tomographic image $B_4$ are projected on the same film as shown in FIGS. 11C and 11D.

The foregoing description relates to the case where four pictures or tomographic images of the affected spot B are separately projected on a single film. Where, however, the affected spot B occupies a relatively large space or two tomographic images well serve the purpose, then the cassette 51 has only to be swung 180°. Where more than four, for example, six to eight tomographic images are separately projected on a single film, such or any other number of tomographic images can be freely projected separately on a single film by proper combination of the displacement of the center of the cassette and the rotation of said cassette 51.

With the cassette-supporting device of FIGS. 6 to 9 constructed as described above, the vertical and horizontal shifting, as well as the rotation, of the cassette 51 are manually carried out. However, it is possible to control these operations by electric motor by converting the rotating force of an electric motor into a linear movement by a mechanism consisting of a combination of, for example, a rack and gear and applying said linear movement to, for example, the first guide shafts 59a, 59b and second guide bearings 62a, 62b and transmitting the rotation of the motor to the rotary drum 64 at a properly reduced speed.

It is impossible for the cassette-supporting device of the above-mentioned arrangement to be fitted with a cassette having any other size than prescribed. To avoid this inconvenience, the undermentioned type of cassette-supporting device may be adopted. Referring to FIGS. 12 and 13, a frame indicated by referential numeral 81 has its outline and thickness so designed as to be supported by the paired cassette-supporting plates 50, 52 shown in FIGS. 4A and 4B. The upper and lower ends of vertically extending guide shafts 82a, 82b are fixed to both horizontal side edges of said frame 81. The guide shafts 82a, 82b are provided with two pairs of guide bearings 84a–84b and 84c–84d which are made to slide axially of said guide shafts 82a, 82b. Both ends of a first cassette-supporting movable rail 83a are fixed to the guide bearings 84a, 84c, and both ends of a second cassette-supporting movable rail 83b are fixed to the guide bearings 84b, 84d. Fixing screws 85a, 85b, 85c, 85d are threadedly engaged with the guide bearings 84a, 84b, 84c, 84d respectively. As the result, the paired movable rails 83a, 83b can slide along the guide shafts 82a, 82b and be brought to rest at any point thereon by the fixing screws 85a, 85b, 85c, 85d.

The mutually facing sides of the paired rails 83a, 83b are provided with grooves for receiving the edge portions of the cassette 51. The opposite sides of the paired rails 83a, 83b to said grooves are fitted with guide members 86a, 86b. The inner wall of the upper part of the frame 81 is fitted with a first fixing guide 87a facing one guide member 86a, and the inner wall of the lower part of the frame 81 is fitted with a second fixing guide 87b facing the other guide member 86b. The guide grooves of the paired rails 83a, 83b and guide members 86a, 86b, 87a, 87b are designed to have such shape and dimensions as to cause the upper or lower edge of the cassette 51 to be inserted sideways into said grooves and guide members and slide therethrough. The vertically extending guide shafts 82a, 82b and movable rails 83a, 83b are impressed with graduations for defining the position of the cassette 51.

The cassette-supporting device of FIGS. 12 and 13 constructed as described above enables a cassette 51 of any size to be kept at any desired position by shifting the movable rails 83a, 83b to any required point and securing them by the fixing screws 85a, 85b, 85c, 85d. For example, where it is desired to place the cassette 51 on the left side of the center of said cassette-supporting device in a horizontal position, then it is advised, as shown in FIG. 14A, to insert the upper and lower edges of the cassette 51 into the grooves of the movable rails 83a, 83b and shift it leftward. Where it is desired to set the cassette 51 at the upper right part of the cassette-supporting device, then it is advised, as shown in FIG. 14B, to hold the cassette 51 between the guide member 86a and first fixing guide 87a.

Referring to FIGS. 15 and 16 showing a modification of the cassette-supporting device of FIGS. 12 and 13, an iron sheet 90 is attached to a frame 81 of the same type as that of FIG. 12 so as to extend across the lengthwise portion of said frame 81. A rectangular movable cassette holder 91 is magnetically attracted to the iron sheet 90. The three sides of said rectangular cassette holder 91, except for the upper side, are provided with engagement projections so as to clamp the cassette 51 therebetween. A pair of magnets 92 vertically spaced from each other are fitted to the backside of the rectangular cassette holder 91. The magnetic attraction of said magnets 92 to the iron sheet 90 attains the tight attachment of the cassette holder 91 to said iron sheet 90.

What we claim is:
1. An X-ray tomography apparatus comprising a seat board for seating an object body for medical examination having a cross section requiring X-ray tomography; an X-ray source for irradiating X-rays toward said examinee's body; rotating film supporting means for holding a film in parallel relationship with the cross section of the examinee's body for photographying X-ray images of the section of the examinee's body through which the X-ray flux passes; rotating collimator means disposed between said X-ray source and said seat board for the body and provided with an opening parallel with the cross section of the examinee's body for restricting the cross section of the X-ray flux emitted from the X-ray source to the desired location and dimensions on the cross section of the body; and a drive mechanism for causing the X-ray source, collimator means, and film to revolve about the examinee's body in the same direction and at the same speed, and also causing the collimator means and film to rotate about their axis at said same speed so that the X-rays are irradiated only onto the body and the film at the same location regardless of the relative rotational position of the X-ray source, collimator means, and film with respect to the examinee's body.

2. An X-ray tomography apparatus according to claim 1, wherein the collimator means is adjustable to vary the cross section of the opening therein.

3. An X-ray tomography apparatus according to claim 1, wherein the drive mechanism comprises a motor; a support shaft rotated by said motor; an arm, the intermediate part of which is connected to one end of said support shaft, one end of which is fitted with the X-ray source with the collimator means fitted to the part of the arm near the X-ray source, and the other end of which is fitted with the film-supporting means; and means for transmitting the rotating moment of the motor to the collimator means and film for their rotation about their axes.

4. An X-ray tomography apparatus according to claim 1, wherein the film-supporting means is a mechanism for detachably supporting a cassette film.

5. An X-ray tomography apparatus according to claim 4, wherein the cassette film has four side edge portions arranged generally in rectangular configuration and the film-supporting means comprises a shaft rotated by the drive mechanism, a first supporting plate fitted perpendicular to the axis of the rotary shaft to hold the cassette film by two opposite side edge portions; a second supporting plate swingably fitted relative to the first supporting plate to hold the cassette film at the other two opposite side edge portions; and a member for keeping the second supporting plate parallel with the first supporting plate.

6. An X-ray tomography apparatus according to claim 5, wherein the first and second film-supporting plates are each provided with a pair of projections at the opposite ends for tightly clamping the side edge portions of the cassette.

7. An X-ray tomography apparatus according to claim 4, wherein the cassette film-supporting mechanism is provided with means for shifting a cassette film fitted thereinto to any desired position.

8. An X-ray tomography apparatus according to claim 7, wherein said cassette film-shifting means comprising a cylindrical member, one end face of which is fitted with the cassette film; a first member for supporting said cylindrical member to permit its axial shifting; a second member for supporting said first member to cause it to be shifted in a direction perpendicular to said axial direction; and a shaft fitted at one end with said second member and rotated by said drive means.

9. An X-ray tomography apparatus according to claim 4, wherein the cassette film-supporting mechanism comprises a shaft rotated by the drive means; a frame fitted to one end of said shaft; a pair of movable cassette-clamping members fitted to said frame in parallel relationship with each other to be moved in one axial direction of said frame, with the cassette designed to be moved between said paired clamping members in the other axial direction perpendicular to said one axial direction.

10. An X-ray tomography apparatus according to claim 9, wherein the cassette film-supporting mechanism comprises a pair of stationary cassette-clamping members secured to the frame in parallel relationship with said movable cassette-clamping members so as to clamp the cassette film between said movable and stationary cassette-clamping members.

11. An X-ray tomography apparatus according to claim 4, wherein the cassette film-supporting mechanism comprises a metal plate rotated by said drive means; and a cassette film holder magnetically attracted to said magnetic plate by which the cassette film is supported.

* * * * *